(12) United States Patent
Bernstein

(10) Patent No.: US 6,972,291 B2
(45) Date of Patent: Dec. 6, 2005

(54) METHOD FOR REDUCING FOOD INTAKE

(76) Inventor: Richard K. Bernstein, 1160 Greacen Point Rd., Mamaroneck, NY (US) 10543-4696

( * ) Notice: Subject to any disclaimer, the term of this patent is extended or adjusted under 35 U.S.C. 154(b) by 134 days.

(21) Appl. No.: 10/187,578

(22) Filed: Jul. 2, 2002

(65) Prior Publication Data
US 2002/0198227 A1 Dec. 26, 2002

(51) Int. Cl.[7] .................... A61K 31/44; A61K 31/485; A61K 31/19
(52) U.S. Cl. .................. 514/282; 514/871; 424/465
(58) Field of Search .............................. 514/282, 871, 514/465; 424/465

(56) References Cited

U.S. PATENT DOCUMENTS

| | | |
|---|---|---|
| 4,217,353 A | 8/1980 | Smith, Jr. |
| 4,478,840 A | 10/1984 | Smith, Jr. |
| 4,573,995 A | 3/1986 | Chen et al. |
| 4,857,533 A | 8/1989 | Sherman et al. |
| 4,863,928 A | 9/1989 | Atkinson et al. |
| 4,877,791 A | 10/1989 | Sherman |
| 4,888,346 A | 12/1989 | Bihari et al. |
| 4,987,136 A | 1/1991 | Kreek et al. |
| 4,994,466 A | 2/1991 | Sherman et al. |
| 5,013,739 A | 5/1991 | Bihari et al. |
| 5,356,900 A | 10/1994 | Bihari et al. |
| 5,716,976 A | 2/1998 | Bernstein |
| 5,727,570 A | 3/1998 | Clemens |
| 5,878,750 A | 3/1999 | Clemens |
| 5,925,768 A | 7/1999 | Barth et al. |
| 6,026,817 A | 2/2000 | Clemens |
| 6,262,062 B1 | 7/2001 | Clemens |
| 6,288,074 B1 | 9/2001 | Bihari |
| 6,306,425 B1 | 10/2001 | Tice et al. |
| 6,344,474 B1 | 2/2002 | Maruani et al. |
| 6,384,044 B1 | 5/2002 | Bihari |
| 6,432,984 B1 | 8/2002 | Barth et al. |

OTHER PUBLICATIONS

"Effects of Naloxone and Naltrexone on Meal Patterns of Freely-Feeding Rats", Kirkham et al. , Biochemistry and Behavior, 1987, 26(3), 515-20.*

"Naltrexone, Serotonin Receptor Subtype Antagonist, and Carbohydrate Intake in Rats", Islam et al., Pharmacology Biochemistry and Behavior, vol. 48, No. 1, pp. 193-201, 1994.*

"Effect of Naltrexone on Food Intake, Hunger, and Satiety in Obese Men", Spiegel et al., abstract, Physiol Behav., 1987; 40(2):135-41.*

Yeomans, M.R., et al., Effects of Naltrexone on Food Intake and Changes in Subjective Appetite Durning Eating: Evidence for Opioid Involvement in the Appetizer Effect, Physiol Behav, 62(1):15-21, Jul. 1997.

Yeomans, M.R., et al., Selective Effects of Naltrexone on Food Pleasantness and Intake, Physiol Behav, 60(2):439-446, Aug. 1996.

de Zwaan, M., et al., Opiate Antagonists and Eating Behavior in Humans: A Review, J Clin Pharmacol, 32(12): 1060-1072, Dec. 1992.

Kraft, K., et al., Long-Term Optiate Receptor Antagonism in a Patient with Panhypopituitarism: Effects on Appetite, Prolactin and Demand for Vasopressin, Horm Metab Res, 23(2):74-75, Feb. 1991.

Bihari, B., et al., Low Dose Naltrexone in the Treatment of Acquired Immune Deficiency Syndrome, Oral Presentation at the IV International AIDS Conference in Stockholm, Jun. 1988.

* cited by examiner

Primary Examiner—Christopher S. F. Low
Assistant Examiner—Brian-Yong S. Kwon
(74) Attorney, Agent, or Firm—Kirkpatrick & Lockhart Nicholson Graham LLP

(57) ABSTRACT

Provided is a method for curbing dietary cravings in a patient, typically a diabetic or obese patient, by administration of a low dose of naltrexone to the patient.

20 Claims, No Drawings

METHOD FOR REDUCING FOOD INTAKE

BACKGROUND OF THE INVENTION

1. Field of the Invention

A method for curbing carbohydrate craving and, in general, overeating through long-term use of low dose naltrexone. The described method finds particular use in treatment of diabetes and obesity.

2. Description of the Related Art

Obesity and diabetes both have reached epidemic proportions. Many obese people are able to effectively reduce their weight by combinations of exercise and/or diet. However, some are not able to reduce their weight on their own and undergo medically supervised diets and/or therapies. Diabetics also can improve their condition by minimizing carbohydrate intake.

A number of low-carbohydrate diet plans make it possible for many diabetics to achieve normal blood sugars. There are, however, three exceptions. The first is gastroparesis, or the partial paralysis of the stomach, and other ailments that can impair stomach emptying. These ailments may include hiatal hernia, stomach or duodenal ulcers, a "tonic" (tight) stomach, gastritis, duodenitis and scleroderma. The second exception is infection. The third exception is the inability to control food intake, especially carbohydrate intake. Because of the "thrifty genotype" or "thrifty phenotype," this condition is expected in many type 2 diabetics.

Indeed, about 25 percent of type 2 diabetic patients find it extremely difficult to remain on a low carbohydrate diet—or indeed any kind of structured diet. Typical scenarios include snacking when bored, eating bread in restaurants for no better reason than it's on the table, and eating everything on their plate regardless of any actual hunger, even when given too-large portions, as is often the case at restaurants. Others may eat a whole pint, and some even a quart of ice cream every night, often when they feel they have nothing else to do. At least 10 percent of type 1 diabetic patients have such problems, but their problems, when they occur, have a more devastating effect on blood sugars. These are the people who rapidly develop retinopathy, neuropathy—for instance numb feet, kidney dysfunction, and so on.

U.S. Pat. No. 5,716,976 discloses the use of a rotation of anorexients to curb carbohydrate addiction. Anorexients are described therein as prescription or nonprescription medications, amino acids, and herbal preparations that can reduce or eliminate carbohydrate craving. Listed anorexients include: serotonin agonists, such as sertraline (ZOLOFT) and fluoxetine (PROZAC); dopamine or norepinephrine agonists, such as levo-dopa, pergoglide (PERMAX), bromocriptine, amphetamines and WELLBUTRIN; phenopropanolamine; centrally acting alpha-2 agonists; certain amino acids, such as tryphophan, 5-hydroxy tryptophan, L-glutamine, L-tyrosine and L-phenylalanine; and herbs, such as ephedra. For long-term suppression of carbohydrate cravings, however, no single anorexiant described in that patent can be used continuously for the long-term because tolerance is developed. Depending on the choice of anorexiant, tolerance can be developed fairly rapidly, for instance in little over a week, or slowly, for instance in as long as six months. The only constant is that tolerance eventually is developed.

Naltrexone, (typically naltrexone hydrochloride (HCl), available generically and under the trade name REVIA) is commonly known as an opioid antagonist. Naltrexone is also related to, naloxone, or n-allylnoroxymorphone. Naltrexone currently is available in 50 mg tablets and is approved by the U.S. Food and Drug Administration (FDA) for treatment of heroin and opium addiction.

High doses of naltrexone (greater than 25 mg) are thought to affect appetite. In U.S. Pat. No. 4,217,353, data is presented that shows naltrexone can elicit a slight anorexic effect in squirrel monkeys at doses of 0.22 mg/kg (corresponding to 22 mg for a 100 kg (220 lb.) person if the data can be directly extrapolated to humans). At higher doses, the anorexic effect was greater. From that data, it was concluded that an effective human dosage might be from 10 to 100 mg per day, with 20 mg, three to four times daily being the preferred dosage. There is no discussion in that patent related to reduction of carbohydrate cravings in monkeys or in humans, especially sufficient reduction of carbohydrate cravings in diabetics. It should be noted that craving of carbohydrates is thought to have a different etiology than traditional hunger and overeating, and might relate to the thrifty genotype or phenotype as described herein.

DeZwaan et al., in "Opiate Antagonists and eating Behavior in Humans: A Review" (1992), J. Clinical Pharmacol. 32:1060–72, summarize a number of studies relating the effect of naltrexone to eating behavior in humans. That article indicates that naltrexone is a long-acting, orally active narcotic antagonist that reduces body weight in animals without evidence of drug tolerance, but that it is risky due to its potential for liver damage. Id. at 1060. The single-dose studies summarized in that review article indicate that short-term doses of naltrexone in amounts of 50 mg or greater affect food intake. In connection with this, however, it is stated that "[t]he doses needed to modulate eating behavior are generally higher than the doses needed to precipitate withdrawal from narcotic alkaloids in humans." Id. at 1068. Long-term studies provided less convincing data that naltrexone would affect appetite and weight gain in humans over the long term. In one study, however, binge eating was affected long-term by 100 mg doses of naltrexone. Later human studies (see, Yeomans et al, "Selective Effects of Naltrexone on Food Pleasantness and Intake" (1996) *Physiology and Behavior* 60(2):439–46 and Yeomans et al., "Effects of Naltrexone on Food Intake and Changes in Subjective Appetite During Eating: Evidence of Opioid Involvement in the Appetizer Effect" (1996) *Physiology and Behavior* 60(1): 15–21 ("Yeomans II")) are ambivalent on the ability of naltrexone at levels of 50 mg to suppress carbohydrate cravings. In Yeomans II, sweet cravings were not reduced by naltrexone, as compared to other food categories.

More recently, the benefits of low-dosage naltrexone for treating a variety of illnesses have become apparent. Low doses of naltrexone are about 25 mg per dose or lower, typically less than about 10 mg per dose and often less than 5 mg per dose. Low doses of naltrexone are suggested for use in treating disease states including: autoimmune disease (U.S. Pat. No. 4,857,533); arthritis and related inflammatory disease (U.S. Pat. No. 4,863,928); interstitial cystitis (U.S. Pat. No. 4,877,791); AIDS/HIV infection (U.S. Pat. No. 4,888,346); gastrointestinal dysmotility (U.S. Pat. No. 4,987,136); multiple sclerosis (U.S. Pat. No. 4,994,466); chronic fatigue syndrome (U.S. Pat. No. 5,013,739); chronic herpes virus infection (U.S. Pat. No. 5,356,900); hyperlipidemia (U.S. Pat. No. 5,727,570); lymphoproliferative syndrome (U.S. Pat. No. 6,288,074); and prostate cancer, as well as other cancers (U.S. Pat. No. 6,384,044). In these references, low dose naltrexone is considered to be less than about 5 mg per dose. In high doses, naltrexone is known as an opioid receptor antagonist. However, low dose naltrexone is thought to act differently, essentially as an agonist, resulting in a relative euphoria similar to the relative euphoria elicited by endorphins (see below and U.S. Pat. No. 4,888,346, column 2, lines 45–61).

To date, there has been no suggestion to use low doses of naltrexone for appetite control, especially for carbohydrate control in humans. Further, there is no suggestion or data showing that such craving will be reduced in diabetics to a level that is sufficient to reduce blood glucose levels to benign, or to more benign levels, particularly in those diabetics who experience substantial carbohydrate cravings. Lastly, there is no indication that low dose naltrexone will be useful for controlling appetite in obese persons and in persons having the thrifty phenotype.

SUMMARY

Therefore, provided herein is a method for controlling carbohydrate cravings in a patient, in which naltrexone is administered to the patient in low doses, preferably at specific times of day so that efficacy of naltrexone peaks before and during times of day when carbohydrate cravings are strongest, such as, without limitation, before and during meals. The described method reduces carbohydrate cravings to assist diabetics in normalizing their blood sugar. Other groups of patients who would benefit from the method described herein are obese persons, persons exhibiting the thrifty phenotype or persons having Syndrome X.

The amount of naltrexone given to a patient in each dose typically is lower than the standard dose of naltrexone used to treat opioid addiction, which is currently available in tablet form in 50 mg doses. Useful low doses of naltrexone for treatment of carbohydrate cravings typically range from about 0.1 mg to about 25 mg from one to five times per day, preferably from about 0.1 mg to less than about 10 mg per dose and most preferably from about 0.1 mg to about 2.5 mg per dose. Dosage requirements will vary from patient to patient and the size of the naltrexone doses and the dosage timing are tailored to fall into a range that provides the patient with sufficient levels of naltrexone effective to curb carbohydrate craving, while, when applicable, keeping the dosage low enough that the patient does not experience typical naltrexone side effects, such as headaches, nausea, loss of libido, diminished pleasure in daily activities and difficulty concentrating on complex tasks (fuzzy thinking).

DETAILED DESCRIPTION

Provided is a method that has had a high success rate in curbing appetite, and especially carbohydrate cravings in patients by administering to the patient a low dose of naltrexone. Efficacy typically is apparent by the second day of treatment. The dosage may be in tablet, caplet or capsule form or may be a controlled-release formulation, such as a slow-release or timed-release formulation. Other delivery methods include transdermal methods, including both passive transdermal systems and active transdermal systems such as iontophoretic systems.

Very strenuous, prolonged physical exercise and climactic sexual activity cause the brain to produce endorphins, also known as the body's own opiates because they are produced endogenously and bind to receptors in the brain that bind actual opiates, such as morphine and codeine. Endorphins cause a pleasant, relaxed feeling, similar to that of narcotics, but to a milder degree and without producing a tolerance. "Tolerance" refers to declining efficacy over time so that higher and higher does are required to produce the same results.

It has been observed that serious runners and many professional athletes tend to prefer protein foods to carbohydrates and do not overeat and become fat as long as they continue their sport. From this, it is hypothesized that endorphins prevent overeating and carbohydrate craving without losing their effect over time as do traditional appetite suppressants.

It has been noted, as mentioned above, that naltrexone, when taken in small doses, appears to either raise endorphin levels in the brain or to act as an endorphin creating an endorphin-like euphoria. Naltrexone was originally introduced because large doses prevented withdrawal symptoms in narcotics addicts attempting to "kick" their habit. In large doses, typically doses of 50 mg or greater, naltrexone will block the brain receptor sites for opiates and endorphins, rendering them ineffective. It has now been found, as shown herein, that small doses of naltrexone are very effective in controlling carbohydrate cravings and addiction, and overeating in general, for a substantial percentage of those who have tried it. Furthermore, just like the endorphins made by athletes, naltrexone, thus far, seems to work for a prolonged period—perhaps indefinitely. Patients who are particularly likely to have carbohydrate cravings and overeating are the obese, the type 2 diabetic and those patients exhibiting the thrifty phenotype.

The thrifty genotype is considered to be an ancient genotype, regulating energy storage in hunter-gatherers society but predisposing for obesity and related diseases, such as diabetes, in industrialized societies where foods, especially carbohydrates, are readily available in unlimited amounts. Recent theories recognize that environment may play a role in the observed phenotype as well as genetics. Thus, the idea of a thrifty genotype may be replaced with the concept of a "thrifty phenotype" in which there are genetic and environmental influences. As used herein, "thrifty phenotype" refers to a person having the outward manifestations of the "thrifty genotype" and/or outward manifestations of related influences.

"Syndrome X," also known as insulin resistance syndrome or the metabolic syndrome, refers to the combination of hypertension, obesity, insulin resistance, dyslipidemia and, often, impaired glucose tolerance, often combined with elevated serum insulin levels.

Naltrexone is preferably administered to act at the time(s) of day when overeating or carbohydrate craving occurs. Naltrexone usually starts working about 3–4 hours after it is taken and continues to work for about six hours, but this timing varies from person to person. If a patient overeats only at supper, she might take a dose about 3–4 hours prior to that meal. If her problem is from after lunch until bedtime, she might take a dose after breakfast, after lunch, and before or after supper, all by trial and error, to find the optimal timing. Different amounts of naltrexone also may be administered at different times, depending on a patient's response to each dosage at each time. If the patient experiences carbohydrate cravings at all waking hours, the patient might take a slow-release (extended-release) or timed-release dose at bedtime that would ideally cover the next morning, or take a dose in the middle of the night if the patient awakens to urinate, as many do. The patient then might take additional doses upon arising, before lunch, mid-afternoon, and after supper or a slow-release dose upon arising. On the other hand, it has been found that certain patients can remain covered by one small dose for more than 24 hours. Finding what works for any given patient's particular pattern of overeating or carbohydrate craving is trial and error. If a patient's problem is only at dinner when she eats out, then she might take the naltrexone about 3–4 hours before the planned dinnertime only on such days.

As used herein, when a dose of naltrexone is said to be taken "before" any event, such as a meal, it is taken at a time adequately prior to that meal to prevent carbohydrate cravings during the meal, and, in a restaurant, at a time to prevent over-ordering. A common time "before" a meal or other event is about 3–4 hours before the meal or event. This time is not definite and can vary from person to person; hence "3–4 hours" is preceded with "about." As used herein, in contrast to taking a dose "before" an event, if a dose is taken "just before" or "just after" an event, it is meant essentially immediately before or after the event to act at a later time, for instance 3–4 hours after the event. As used herein, "dietary cravings" are cravings that cause a person to overeat such that the person eats more than he or she needs in order to maintain a healthy body weight and/or healthy blood glucose levels.

As seen below, certain patients have discontinued low-dose naltrexone therapy because of uncomfortable side effects. These effects included tiredness, headache, nausea, impaired libido, diminished pleasure in daily activities and difficulty concentrating on complex tasks. Such problems nearly always occur after the first dose or a dosage increase. When they occur, the dose of naltrexone must either be lowered or naltrexone therapy must be discontinued if lower doses are ineffective.

As with any medication, although not necessary, it is wise to start naltrexone at the lowest possible dose and to then increase the dose as necessary. The importance of fine-tuning this medication is illustrated by the true case of an obese lady who got a headache with one 4 mg capsule. At a dose of 2 mg, she had no headache but her appetite was unaffected. Finally, at a 3 mg dose, her cravings were curbed and she had no headache.

Another side effect that some patients relate is a feeling of mental confusion that impairs concentration upon difficult tasks. Like a headache, this effect is unacceptable. For this reason, a patient typically is started on a very low dose—for example, and without limitation, 1 mg capsules—and the amount of each dose is then increased or decreased until an effective level is reached at which the patient experiences no side effects.

As used in the examples herein, "naltrexone" refers to naltrexone HCl. Naltrexone HCl is the only naltrexone salt listed in the FDA Orange Book. Nevertheless, "naltrexone," as used generally herein, also refers equally to any other pharmaceutically acceptable forms of naltrexone.

Naltrexone may be provided in standard 50 mg tablet form, such as is commercially available either generically or under the trade name REVIA. The commercially available tablets may be divided to provide the desired dose. For instance, a 50 mg tablet may be halved to produce about a 25 mg dose.

As indicated herein, the dose of naltrexone may be 0.25 mg or less. Because commercially available tablets typically can only be halved, in cases where doses are less than 25 mg, commercially available tablets may be compounded into suitable tablets or capsules as follows, and/or by other methods as are well known in the art. A compounding chemist typically grinds the commercially available tablets and dilutes the naltrexone using any pharmaceutically acceptable excipients, binders, fillers, sweeteners, coloring agents, lubricants or other conventional additives. The diluted naltrexone is then placed in a capsule for oral ingestion, for example in 0.25, 0.5, 1, 2, 4, 6, 8, 10 or 12 mg doses.

Slow- or sustained-released, (collectively, "controlled release") naltrexone formulations also can be useful to control the timing of the release of naltrexone. As mentioned above, timed-release formulations might be useful for patients who crave carbohydrates in the morning. The patient would take a timed release capsule or tablet that would delay delivery of effective amounts of naltrexone for a number of hours, such as about eight hours, so that the patient could take timed-release naltrexone before bed, and experience suppression of carbohydrate cravings upon awakening in the morning. A slow-release formulation would be particularly useful for those patients who crave carbohydrates all day long. In such a case, naltrexone would be slowly released over a long period of time, for instance, and without limitation, 0.25–50 mg over 6–18 hours, to suppress carbohydrate cravings for most, or all, waking hours.

Methods for formulating timed- or slow-release tablets are well known to those of ordinary skill in the art of drug-delivery. Examples of controlled-release formulations include, without limitation: sugar or polymer-coated tablets, caplets or capsules; coated or matrixed naltrexone particles incorporated in a capsule; incorporation of naltrexone in a slowly dissolving tablet matrix; osmotic pumps; and transdermal devices, including, iontophoretic devices. These are methods, among many, that can be used to produce desired naltrexone delivery profiles, different from the standard immediate-release tablet or liquid compositions.

The naltrexone also may be provided in liquid form. One liquid formulation is disclosed in U.S. Pat. No. 4,888,346, in which 50 mg naltrexone tablets are ground and are dissolved in heavy cherry-flavored syrup. Formulating naltrexone in liquid form may be especially useful during tailoring the dose of naltrexone. When naltrexone is provided in capsule form, to change the dose, a new capsule having a different amount of naltrexone often has to be made. When the naltrexone is in liquid form, the dosage can be adjusted by dispensing different volumes of naltrexone, thereby removing the need to re-formulate the naltrexone when a new dose is prescribed. For instance, naltrexone may be provided at a concentration of 1 mg per cc. As a result, dosage may be adjusted in 1 mg increments for every cc taken. Once an optimal dose is determined, the patient has the option of having tablets formulated, or continuing taking naltrexone in liquid form.

It should be noted that these are examples of suitable dosage forms. A plethora of additional dosage forms are known to those of skill in the art of drug delivery and opioid antagonist delivery, including compounding pharmacists, and may be suitable for providing suitable naltrexone delivery profiles. These other formulations include, without limitation tablets, capsules, caplets, liquids, oil/water emulsions, coated particles, transdermal devices, injectable formulations and suppositories. U.S. Pat. No. 6,306,425 describes injectable extended-release naltrexone microspheres. However, injectable forms likely will not find use in the daily treatment of carbohydrate craving in most patients, who would not wish to be injected regularly. U.S. Pat. No. 4,573,995 describes a transdermal system for the delivery of naltrexone. Transdermal patches currently are available for the extended release of drugs over many days.

EXAMPLES

Fifty mg naltrexone tablets (REVIA) were ground, mixed with lactose and dispensed at lower doses into capsules by a compounding chemist according to standard methods in doses indicated in the following examples.

For each patient described below, the patient was given an initial dose and the dose was then tailored to the patient. The dose of naltrexone was lowered when the patient experienced side effects, including headaches, nausea and/or difficulty concentrating on complex tasks, or if naltrexone is inadequately effective at a higher dose. It should be noted that lower doses are sometimes more effective than higher doses. However, the dosage was maintained at levels that resulted in curbing of carbohydrate craving. Although "final" values are provided, the study continues unless termination is indicated. The following patients, as well as additional patients are currently being studied. All patients were treated for at least two months, unless released from the study due to adverse effects that were not relieved by reducing the dosage of naltrexone.

The "rating" of naltrexone efficacy is a subjective scale of zero to ten. A value of zero means that the patient experiences no beneficial effects upon food or carbohydrate craving when taking naltrexone. A value of ten means that the patient experiences no food or carbohydrate craving after taking naltrexone, and can maintain control even when a tantalizing carbohydrate-laden treat, such as a hot buttered roll, a cookie or ice cream, is placed in front of the patient, even when the patient is hungry. For diabetics, a value of eight or greater is considered a success. In contrast, for obese, non-diabetics, a value of six or greater is considered a success because carbohydrates need to be controlled, but not as diligently controlled as with diabetics.

Of note, one patient who snacked between dinner and bedtime also had insomnia. Since naltrexone made him tired, we were able to use it to treat his insomnia and his snacking simultaneously. Unless otherwise noted, all patients are diabetics. Patients who experienced a naltrexone efficacy rating of greater than or equal to 8 also experienced a suppression of both carbohydrate craving and any tendency to overeat, in general.

Example 1

Patient 1 was a 45-year-old male with an initial weight of 207.5 lbs. His initial dosage of naltrexone HCl was 12.5 mg twice daily, which was tailored to 1 mg three times daily over the course of the study. Patient 1 experienced a naltrexone efficacy rating of ≧8, but discontinued treatment because he experienced headaches, even at the final dosage.

Example 2

Patient 2 was a 42-year-old female with an initial weight of 256 lbs. Her initial dosage of naltrexone HCl was 12.5 mg per day (mg/d), which was tailored to 12.5 mg four times per day over the course of the study. During the study, Patient 2 experienced a naltrexone efficacy rating of 7 to 8. She continues using naltrexone to curb her carbohydrate cravings.

Example 3

Patient 3 was a 58-year-old male with an initial weight of 252 lbs. His initial dosage of naltrexone HCl was 12.5 mg when eating out, which was tailored to 2 mg twice daily over the course of the study. Patient 3 experienced a naltrexone efficacy rating of ≧8. He continues using naltrexone to curb his carbohydrate cravings.

Example 4

Patient 4 was a 57-year-old non-diabetic female with an initial weight of 183 lbs. Her initial dosage of naltrexone HCl was 8 mg twice daily, which was adjusted to 25 mg three times daily over the course of the study. Patient 4 experienced a naltrexone efficacy rating of 4, and discontinued treatment because she experienced headaches.

Example 5

Patient 5 was a 51-year-old female with an initial weight of 162 lbs. Her initial dosage of naltrexone HCl was 8 mg after lunch, which remained unchanged over the course of the study. Patient 5 experienced a naltrexone efficacy rating of 10. She continues using naltrexone to curb her carbohydrate cravings.

Example 6

Patient 6 was a 43-year-old male with an initial weight of 204 lbs. His initial dosage of naltrexone HCl was 6 mg twice daily, which was tailored to 1 mg twice a day over the course of the study. Patient 6 experienced a naltrexone efficacy rating of 10. He continues using naltrexone to curb his carbohydrate cravings.

Example 7

Patient 7 was an 18-year-old female suffering from polycystic ovarian syndrome with an initial weight of 170 lbs. Her initial dosage of naltrexone HCl was 6 mg three times daily, which was tailored to 36 mg/d over the course of the study (6 mg in the morning, 12 mg with lunch and 18 mg at about 3:00 P.M.). Patient 7 experienced a naltrexone efficacy rating of 8 to 9. She continues using naltrexone to curb her carbohydrate cravings.

Example 8

Patient 8 was a 43 year-old male with an initial weight of 182 lbs. His initial dosage of naltrexone HCl was 8 mg after lunch, which was tailored to 8 mg four times daily over the course of the study. Patient 8 experienced a naltrexone efficacy rating of 9.5. He continues using naltrexone to curb his carbohydrate cravings.

Example 9

Patient 9 was a 58-year-old female with an initial weight of 106 lbs. Her initial dosage of naltrexone HCl was 25 mg/d, which was tailored to 50 mg/d over the course of the study. Patient 9 experienced a naltrexone efficacy rating of <8. Patient 9 discontinued the study before low doses of naltrexone were tried.

Example 10

Patient 10 was a 35-year-old female with an initial weight of 161 lbs. Her initial dosage of naltrexone HCl was 12.5 mg three times daily, which was adjusted to 50 mg three times daily over the course of the study. Patient 10 experienced a naltrexone efficacy rating of zero, but doses of naltrexone less than 12.5 mg were not tried.

Example 11

Patient 11 was a 34-year-old-male with an initial weight of 183 lbs. His initial dosage of naltrexone HCl was 8 mg/d, which was tailored to 32 mg/d (8 mg in the morning, 16 mg just after lunch and 8 mg just before dinner) over the course of the study. Patient 11 experienced a naltrexone efficacy rating of ≧8. He continues using naltrexone to curb his carbohydrate cravings.

Example 12

Patient 12 was a 54-year-old female with an initial weight of 114 lbs. Her initial dosage of naltrexone HCl was 4 mg after lunch, which was tailored to 4.5 mg over the course of the study. Patient 12 experienced a naltrexone efficacy rating of zero, and discontinued treatment because she experienced headaches, even at the final dosage.

Example 13

Patient 13 was a 51-year-old male with an initial weight of 208 lbs. His initial dosage of naltrexone HCl was 5 mg three times per day, which was tailored to 8 mg twice per day over the course of the study. Patient 13 experienced a naltrexone efficacy rating of 8.5. He continues using naltrexone to curb his carbohydrate cravings.

Example 14

Patient 14 was a 59-year-old male with an initial weight of 226.5 lbs. His initial dosage of naltrexone HCl was 0.1 mg nine times per day, which was adjusted to 50 mg three times daily over the course of the study. Patient 14 experienced a carbohydrate craving rating of zero.

Example 15

Patient 15 was a 51-year-old male with an initial weight of 184.25 lbs. His initial dosage of naltrexone HCl was 0.75 mg twice daily, which was tailored to 0.25 mg twice daily. He experienced multiple side effects, including decreased libido, confusion, diminished animation and excessive loss of appetite at the initial dose, but not at the final dose. Patient 15 experienced a naltrexone efficacy rating of 10. He continues using naltrexone to curb his carbohydrate cravings.

These data illustrate that a significant percentage of patients realized significant reductions in carbohydrate cravings by taking naltrexone in substantially lower doses than is used to treat opioid addiction. Many patients who report success take between about 0.25 mg and about 25 mg one to five times daily, more typically about 0.25 mg to about 10 mg one to four times daily. A number of patients responded very well, with substantial reduction in appetite and carbohydrate craving on dosages of from about 0.25 mg to about 8 mg one to three times daily, with a total daily intake of about 8 mg or less, and even 2 mg or less.

I claim:

1. A method for reducing food intake in a human patient, comprising administering to the patient a dose of naltrexone in the range of about 0.1 to 12.5 mg one to five times daily with a maximum daily dose of 12.5 mg.

2. The method of claim 1, wherein each dose of naltrexone ranges from about 0.25 mg to about 2.5 mg.

3. The method of claim 1, wherein the naltrexone is administered as a controlled-release dosage form.

4. The method of claim 1, wherein the naltrexone is administered orally.

5. The method of claim 1, wherein the naltrexone is administered transdermally.

6. The method of claim 1, wherein the naltrexone is administered to the patient before a meal.

7. The method of claim 1, wherein the naltrexone is administered to the patient before a time of day the patient typically craves carbohydrates.

8. The method of claim 1, wherein the naltrexone is administered to the patient about three to four hours before a time of day the patient typically craves carbohydrates.

9. The method of claim 1, wherein the patient is obese.

10. The method of claim 1, wherein the naltrexone is administered to a patient for at least about three months.

11. A method of reducing food intake in a patient, comprising administering to the patient from about 0.25 mg to about 10 mg naltrexone per dose with a maximum daily dose of 12.5 mg.

12. The method of claim 11, wherein the daily dose of naltrexone is about 8 mg or less.

13. The method of claim 11, wherein each dose of naltrexone is about 2.5 mg or less.

14. The method of claim 11, wherein the naltrexone is administered as a timed-release dosage form.

15. The method of claim 11, wherein the naltrexone is administered to the patient before a meal.

16. The method of claim 11, wherein the naltrexone is administered to the patient before a time of day the patient typically overeats.

17. The method of claim 11, wherein the naltrexone is administered to the patient about three to four hours before a time of day the patient typically overeats.

18. The method of claim 11, wherein the naltrexone is administered to a patient for at least three months.

19. The method of claim 1, wherein at least one of the daily doses of naltrexone is administered to the patient at bedtime.

20. The method of claim 11, wherein at least one of the daily doses of naltrexone is administered to the patient at bedtime.

* * * * *